(12) United States Patent
Wycoff et al.

(10) Patent No.: US 9,669,241 B2
(45) Date of Patent: Jun. 6, 2017

(54) WATERLESS ANIMAL BATH

(71) Applicant: Sirius Products, Inc., Longmont, CO (US)

(72) Inventors: Jeffrey Wycoff, Boulder, CO (US); Don E. Reynolds, Athens, TN (US)

(73) Assignee: Ascent IP Holdings, LLC, Longmont, CO (US)

( * ) Notice: Subject to any disclaimer, the term of this patent is extended or adjusted under 35 U.S.C. 154(b) by 149 days.

(21) Appl. No.: 14/187,072

(22) Filed: Feb. 21, 2014

(65) Prior Publication Data

US 2014/0242021 A1    Aug. 28, 2014

Related U.S. Application Data

(60) Provisional application No. 61/768,376, filed on Feb. 22, 2013.

(51) Int. Cl.
| | | |
|---|---|---|
| *A61K 8/97* | (2006.01) | |
| *A61Q 5/02* | (2006.01) | |
| *A61K 8/33* | (2006.01) | |
| *A61K 8/44* | (2006.01) | |
| *A61K 8/49* | (2006.01) | |
| *A61Q 17/00* | (2006.01) | |
| *A61Q 17/02* | (2006.01) | |
| *A61Q 19/10* | (2006.01) | |
| *A61K 8/92* | (2006.01) | |

(52) U.S. Cl.
CPC .................. *A61Q 5/02* (2013.01); *A61K 8/33* (2013.01); *A61K 8/44* (2013.01); *A61K 8/4993* (2013.01); *A61K 8/922* (2013.01); *A61Q 17/005* (2013.01); *A61Q 17/02* (2013.01); *A61Q 19/10* (2013.01)

(58) Field of Classification Search
CPC ........ A01N 25/02; A01N 35/04; A01N 65/28; A01N 65/44; A01N 25/06; A01N 65/22; A01N 65/24; A01N 27/00; A01N 31/02; A01N 31/04; A61K 36/28; A61K 36/47; A61K 8/37; A61K 8/97; A61K 8/922; A61K 2800/262; A61K 2800/594; A61K 8/22; A61K 8/45; A61K 8/46; A61K 8/673; A61K 8/8152; A61K 8/84; A61K 8/86; A61K 8/896; A61Q 8/05; A61Q 5/00; A61Q 5/004; A61Q 5/06; A61Q 7/00; A61Q 9/02

See application file for complete search history.

(56) References Cited

U.S. PATENT DOCUMENTS

| | | | |
|---|---|---|---|
| 4,035,267 A | | 7/1977 | Gleckler et al. |
| 5,826,546 A | * | 10/1998 | Epstein ................ A01K 13/001 |
| | | | 119/651 |
| 5,872,087 A | | 2/1999 | Neelakantan |
| 6,114,298 A | | 9/2000 | Petri et al. |
| 7,393,528 B2 | | 7/2008 | Tvedten |
| 8,293,286 B2 | | 10/2012 | Nouvel |
| 8,449,895 B1 | | 5/2013 | Koiteh |
| 8,586,105 B2 | | 11/2013 | Anderson |
| 8,637,489 B2 | | 1/2014 | Van Nguyen et al. |
| 2004/0234489 A1 | * | 11/2004 | Muller .................... A61K 8/365 |
| | | | 424/70.22 |
| 2008/0031907 A1 | * | 2/2008 | Tamarkin ............... A61K 8/046 |
| | | | 424/401 |
| 2012/0282190 A1 | | 11/2012 | Hammer |
| 2013/0344022 A1 | | 12/2013 | Anderson et al. |
| 2015/0104348 A1 | * | 4/2015 | Nichols ..................... A61L 9/01 |
| | | | 422/5 |

FOREIGN PATENT DOCUMENTS

| | | |
|---|---|---|
| WO | WO 92/21320 | 12/1992 |
| WO | WO 2009/130714 | 10/2009 |

OTHER PUBLICATIONS

U.S. Appl. No. 61/768,376, filed Feb. 22, 2013.

* cited by examiner

*Primary Examiner* — Nannette Holloman
(74) *Attorney, Agent, or Firm* — Craig R. Miles; CR MILES P.C.

(57) ABSTRACT

Generally, compositions which can be applied to hair, fur or skin of an animal and are useful for reducing, removing or eliminating undesirable materials or odors or parasites ("extraneous matter") from the hair, fur or skin of the animal. Specifically, compositions which can be applied to hair, fur or skin of an animal and can reduce, remove or eliminate undesirable materials or odors or parasites ("extraneous matter") from the hair, fur or skin of the animal without a need of a rinse composition.

11 Claims, 4 Drawing Sheets

FIG. 2

| RAW MATERIAL | WEIGHT PERCENT | RANGE PERCENT |
|---|---|---|
| WATER | 98.56 | 80.00 TO 99.97 |
| SURFACTANT | 1.000 | 0.100 TO 5.000 |
| LEMONGRASS OIL CONTAINING CITRAL | 0.040 | 0.010 TO 10.00 |
| CHELATING AGENT | 0.400 | 0.100 TO 5.000 |

FIG. 3

| RAW MATERIAL | WEIGHT PERCENT | RANGE PERCENT |
|---|---|---|
| WATER | 98.56 | 80.00 TO 99.97 |
| SURFACTANT | 1.000 | 0.100 TO 5.000 |
| LEMONGRASS OIL CONTAINING CITRAL | 0.040 | 0.010 TO 10.00 |
| CHELATING AGENT | 0.400 | 0.100 TO 5.000 |
| COATING AGENT | 1.500 | 0.100 TO 10.00 |
| CONDITIONING AGENT | 7.250 | 0.100 TO 20.00 |
| PRESERVATIVE | 0.100 | 0.001 TO 5.000 |
| FRAGRANCE | 0.015 | 0.000 TO 1.000 |
| COLORING AGENT | 0.015 | 0.000 TO 1.000 |
| pH CONTROL AGENT | 0.010 | 0.000 TO 1.000 |

FIG. 4

| RAW MATERIAL | WEIGHT PERCENT | RANGE PERCENT |
|---|---|---|
| WATER | 89.695 | 68.85 TO 98.12 |
| TRILON M LIQUID | 0.400 | 0.200 TO 0.600 |
| ARYLESSENCE MOD AF 151615 | 0.015 | 0.005 TO 0.200 |
| LEMONGRASS OIL | 0.040 | 0.010 TO 0.500 |
| TWEEN 20 | 0.500 | 0.100 TO 1.000 |
| ETHOX DO-9 | 0.500 | 0.300 TO 2.000 |
| MASIL EM 10000 C | 1.500 | 0.200 TO 10.00 |
| JOJOBA OIL | 0.100 | 0.050 TO 0.200 |
| PROPYLENE GLYCOL | 7.050 | 1.000 TO 15.00 |
| ACTISEA 100 | 0.100 | 0.010 TO 1.500 |
| KATHON CG/ICP | 0.100 | 0.005 TO 0.150 |

FIG. 5

| RAW MATERIAL | WEIGHT PERCENT | RANGE PERCENT |
|---|---|---|
| WATER | 90.36 | 71.10 TO 98.56 |
| VERSENE 100 CHELATING AGENT | 0.250 | 0.050 TO 0.600 |
| ARYLESSENCE MOD AF 151615 | 0.040 | 0.010 TO 0.400 |
| TWEEN 20 | 0.500 | 0.100 TO 1.000 |
| DOW CORNING 200 FLUID | 1.500 | 0.200 TO 10.00 |
| JOJOBA OIL | 0.100 | 0.050 TO 0.200 |
| PROPYLENE GLYCOL | 7.050 | 1.000 TO 15.00 |
| ACTISEA 100 | 0.100 | 0.010 TO 1.500 |
| DOWICIL 75 PRESERVATIVE | 0.100 | 0.020 TO 0.200 |

WATERLESS ANIMAL BATH

This United States Non-Provisional Patent Application claims the benefit of U.S. Provisional Patent Application No. 61/768,376, filed Feb. 22, 2013, hereby incorporated by reference herein.

I. FIELD OF THE INVENTION

Generally, compositions which can be applied to hair, fur or skin of an animal and are useful for reducing, removing or eliminating undesirable materials, odors or parasites ("extraneous matter") from the hair, fur or skin of the animal. Specifically, compositions which can be applied to hair, fur or skin of an animal and can reduce, remove or eliminate undesirable materials, odors or parasites ("extraneous matter") from the hair, fur or skin of the animal without a need for a discrete rinse composition.

II. BACKGROUND OF THE INVENTION

Conventional shampoo products used for cleansing the hair, fur or skin of an animal may require use of a discrete rinse composition for initial wetting or soaking of the hair, fur or skin of the animal prior to or during application. Additionally, conventional shampoos may require use of a discrete rinse composition, such as water, for removal of the conventional shampoo product from the hair, fur or skin of the animal. If certain components of conventional shampoo products are not removed from the hair, fur or skin of the animal, these components may adversely affect the animal, causing skin irritation, attracting undesired materials, odors, or parasites, dulling sheen of the hair or fur, or the like.

As conventional shampoo products may require use of a discrete rinse composition for application to and removal from the hair, fur or skin of an animal, there can be significant challenges associated with bathing animals using these conventional shampoo products. For example, bathing animals using a discrete rinse composition may be impractical due to physical location, availability of a discrete rinse composition, weather conditions, travel, or due to the circumstance of the animal relating to a medical condition, such as a skin condition, allergy, temperament, or the like.

Additionally, conventional shampoo products may not be effective in repelling parasites, for example fleas or ticks, after the conventional shampoo is rinsed and the hair, fur or skin of the animal dries.

The inventive compositions afford advantages which address each of the above described problems with conventional shampoo products.

III. SUMMARY OF THE INVENTION

Accordingly, a broad object of the invention can be to provide inventive compositions which can be applied to hair, fur or skin of animals to reduce, remove, or eliminate undesirable materials, odors or parasites (herein after referred to collectively as "extraneous matter") from the hair, fur or skin of the animal without a need for a discrete rinse composition to remove the inventive composition from the hair, fur, or skin.

Another broad object of the invention can be to provide a method of producing a composition for animals, useful for reducing, removing, or eliminating undesirable materials, odors or parasites from the hair, fur or skin of the animal without a need for a discrete rinse composition.

Another broad object of the invention can be to provide a method of bathing an animal using an inventive composition useful for reducing, removing, or eliminating undesirable materials, odors or parasites from the hair, fur or skin of the animal without a need for a discrete rinse composition.

Naturally, further objects of the invention are disclosed throughout other areas of the specification, drawings, and claims.

IV. BRIEF DESCRIPTION OF THE DRAWINGS

FIG. 2 is a table which lists raw materials of particular embodiments of the inventive composition.

FIG. 3 is a table which lists raw materials of particular embodiments of the inventive composition.

FIG. 4 is a table which lists raw materials of particular embodiments of the inventive composition.

FIG. 5 is a table which lists raw materials of particular embodiments of the inventive composition.

V. DETAILED DESCRIPTION OF THE INVENTION

Figure 1:
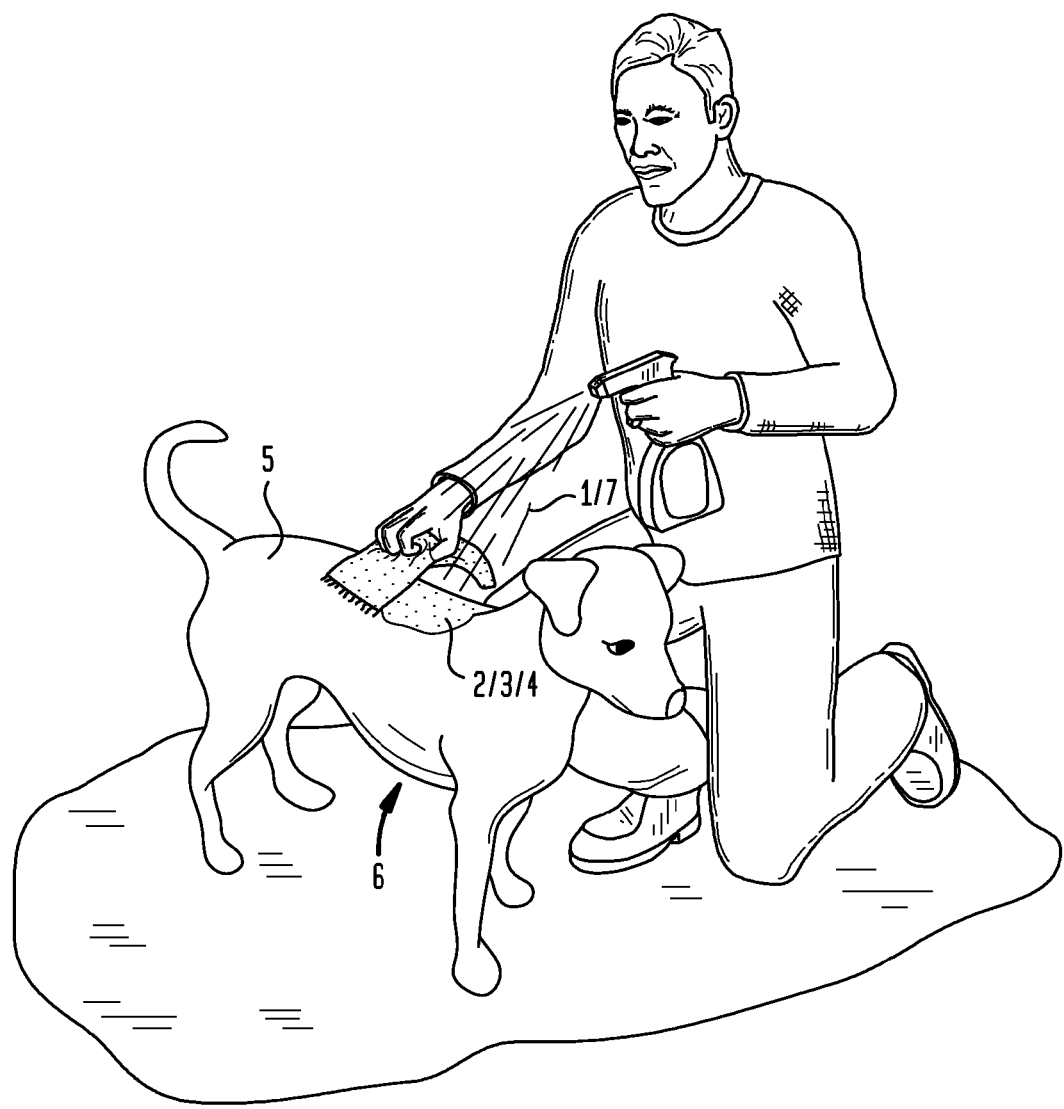
FIG. 1 shows an exemplary method of applying and removing embodiments of the inventive composition to the hair, fur or skin of an animal.

Now referring primarily to FIG. 1, a method of using a particular embodiment of the inventive composition (1) can be understood, which can be used to reduce, remove, or eliminate extraneous matter, such as undesirable materials (2), odors (3), parasites (4), or the like associated with the hair, fur or skin (5) of an animal (6). Embodiments of the inventive composition (1) can be applied as a solution or suspension directly or indirectly to the hair, fur or skin (5) of an animal (6). As an illustrative example, particular embodiments can be applied in the form of a stream or spray (7). Following application, the inventive composition (1) can be distributed on the hair, fur or skin (5) of the animal (6) by mechanical action such as rubbing, brushing, combing, or the like. Following distribution, a portion of the inventive composition (1) can be removed from the hair, fur or skin (5) of the animal (6) without the use of a discrete rinse composition. Removal of embodiments of inventive compositions (1) from the hair, fur, or skin (5) of an animal (6) without use of discrete rinse compositions can be achieved by brushing, toweling dry, blow drying, or the like, or combinations thereof.

The term "rinse composition" for the purposes of this invention means any amount of liquid discrete from the liquid included in the inventive composition (1) itself, regardless of the manner of use, such as water.

Where trade names or trademarks are utilized herein, whether in Table 1 through Table 4 or FIG. 2 through FIG. 5, or any table, figure, or portion of the description, the trade name material or the trademark material is understood to have the chemicals or ingredients in the amounts or combinations as described below. The trade name material or trademark material or a substantially equivalent product or combination of chemicals or ingredients can be utilized in embodiments of the inventive compositions (1). It is further understood that where a trade name material or trademark material is utilized in a Table or Figure that substantially equivalent chemicals or ingredients in the amounts and combinations as indicated below can be utilized in substitution of the trade name material or trademark material. A person of ordinary skill in the art can convert the weight percentages shown in the Tables or Figures to determine the amount of each chemical or ingredient to mix when the equivalent of the trade name material or trademark material is prepared.

Where the constituents of a particular trade name material or trademark material have been set out a first time in the description below, each applies to the subsequent uses of the trade name material or trademark material in the description, Tables and Figures.

Now referring primarily to FIG. 2 and Table 1, embodiments of the inventive composition (1) can include an amount of water, an amount of chelating agent, an amount of citral and an amount of surfactant.

TABLE 1

| Raw Material | Weight Percent | Range Percent |
|---|---|---|
| Water | 98.56 | 80.00 to 99.97 |
| Surfactant | 1.000 | 0.100 to 5.000 |
| Lemongrass oil containing citral | 0.040 | 0.010 to 10.00 |
| Chelating agent | 0.400 | 0.100 to 5.000 |

The amount of surfactant can be provided in a range of between about 0.1% to about 5% by weight percent of the inventive composition (1). The amount of surfactant can be selected from the group including or consisting of: between about 0.1% to about 1.0% by weight of said composition, between about 0.5% to about 1.5% by weight of said composition, between about 1.0% to about 2.0% by weight of said composition, between about 1.5% to about 2.5% by weight of said composition, between about 2.0% to about 3.0% by weight of said composition, between about 2.5% to about 3.5% by weight of said composition, between about 3.0% to about 4.0% by weight of said composition, between about 3.5% to about 4.5% by weight of said composition, and between about 4.0% to about 5.0% by weight of said composition.

As to particular embodiments of the inventive composition (1), there can be an advantage in including a lesser amount of surfactant in the inventive composition (1). The amount of surfactant can be sufficient to allow combination of the chemicals and ingredients within an embodiment which correspondingly reduces the amount of inventive composition (1), or components thereof, residual on the hair, fur or skin (5) of an animal (6) (referred to as "composition residue") following removal of the inventive composition (1) from the hair, fur or skin (5) of the animal (6) without the use of a discrete rinse composition, thereby avoiding conditions that can result from residual composition and, in particular, residual amounts of surfactant.

Accordingly, embodiments of the inventive composition (1) can be formulated to reduce the amount of composition residue which remains on the hair, fur or skin (5) of an animal (6) following removal of a portion of the inventive composition (1) from the hair, fur, or skin (5) of the animal (6) without the use of a discrete rinse composition by including a reduced or minimal amount of surfactant in embodiments of the inventive composition (1) itself. Such a reduced or minimal amount of surfactant comprises an amount of surfactant sufficient to allow stable combination (reducing or avoiding the tendency of the chemicals or ingredients to separate during the normal duration of storage) or allow the application of cleaning the hair, fur or skin (5) of an animal (6). A lesser amount of surfactant as compared to conventional shampoo products can be included in particular embodiments of the inventive composition (1) which allows use of particular embodiments of the inventive composition (1) to be used without a discrete rinse composition.

Illustrative embodiments, can include or consist of an amount of surfactant of about 0.5% by weight percent of the inventive composition (1); as such, the amount of composition residue which remains on the hair, fur or skin (5) of an animal (6) following the application and subsequent removal can be similar or lesser than that compared to conventional shampoo products even without use of a discrete rinse composition. The amounts of surfactant useful in various embodiments of the present invention can vary depending upon the particular surfactant and other chemicals or ingredients used in a particular embodiment of the inventive composition (1).

Examples of suitable surfactants encompassed by the inventive composition (1) can include or be selected from the group consisting of: anionic surfactants, cationic surfactants, nonionic surfactants, zwitterionic surfactants, and combinations thereof.

As to particular embodiments, the anionic surfactants can include or be selected from the group consisting of: alkyl sulfates, alkyl ether sulfates, alkaryl sulfonates, alkyl sulfosuccinates, n-alkyl sarcosinates, alkyl phosphates, alkyl ether phosphates, alkyl ether carboxylates, alpha-olefin sulfonates, or the like, or combinations thereof. Alkyl groups generally can contain from about 8 to about 18 carbon atoms and can be saturated or unsaturated. Alkyl ether sulfates, alkyl ether phosphates and alkyl ether carboxylates can contain from about 1 to about 10 ethylene oxide units per molecule. In a further example, particular anionic surfactants can include or be selected from the group consisting of: sodium lauryl sulfate, sodium laureth sulfate, ammonium lauryl sulfate, ammonium laureth sulfate, disodium laureth sulfosuccinate, disodium ricinoleamido monoethanolamide sulfosuccinate, sodium cocoyl isethionate, sodium methyl oleoyl taurate, sodium methyl cocoyl taurate, sodium laureth-13 carboxylate, sodium C14-16 olefin sulfonate, sodium laureth-4 phosphate, laureth-3 phosphate, triethylanolamine lauryl sulfate, magnesium lauryl sulfate, sodium tridecyl sulfate, alpha-olefin sulfate, or the like, or combinations thereof. In yet a further example, particular anionic surfactants can include ammonium laureth sulfate, ammonium lauryl sulfosuccinate, triethanolamine lauryl sulfate, or the like, or combinations thereof.

Examples of cationic surfactants suitable for use in embodiments can include or be selected from the group consisting of: cationic functional groups such as: octenidine dihydrochlorides, alkyltrimethylammonium salts, cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide, or the like, or combinations thereof.

Examples of nonionic surfactants suitable for use with embodiments can include or be selected from the group consisting of: alkoxylated derivatives of the following: fatty alcohols, alkyl phenols, fatty acids, fatty acid esters, fatty acid amides, or the like, or combinations thereof.

Additional examples of nonionic surfactants suitable for use in embodiments can include or be selected from the group consisting of: alkyl glycosides, which can be represented by the formula $(S)_n$—O—R wherein S is a sugar moiety such as glucose, fructose, mannose, galactose, and the like; n is an integer from 1 to 1000, and R is a C8-C30 alkyl group. Non-limiting examples of long chain alcohols from which the alkyl group can be derived include decyl alcohol, cetyl alcohol, stearyl alcohol, lauryl alcohol, myristyl alcohol, oleyl alcohol, or the like, or combinations thereof.

Yet additional examples of nonionic surfactants suitable for use in embodiments can include or be selected from the group consisting of: sucrose ester surfactants, glyceryl esters and polyglyceryl esters, including for example, glyceryl monoesters, including glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and combinations thereof, and polyglyceryl esters of C16-C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, or the like, or combinations thereof.

Still yet additional examples of nonionic surfactants suitable for use in embodiments can include or be selected from the group consisting of: sorbitan esters, including sorbitan esters of C16-C22 fatty acids, or the like, or combinations thereof.

Still yet additional examples of nonionic surfactants suitable for use in embodiments can include or be selected from the group consisting of: alkoxylated derivatives of glyceryl esters, sorbitan esters, and alkyl polyglycosides, wherein the alkoxy groups can include C2-C6 oxides and their mixtures, with ethoxylated or propoxylated derivatives of these materials being typical. Nonlimiting examples of ethoxylated materials can include ethoxylated sorbitan mono-, di- and/or tri-esters of C12 to C18 fatty acids with an average degree of ethoxylation of from 2 to 20, such as polysorbate 20 ($C_{58}H_{114}O_{26}$, CAS No: 9005-64-5), or the like, or combinations thereof.

Examples of zwitterionic (amphoteric) surfactants suitable for use with embodiments can include or be selected from the group consisting of: sultaines (such as cocamidopropyl hydroxy sultaine); glycinates (such as cocoamphocarboxyglycinates); glycines (such as cocoamidopropyldimethylglycine); propionates (such as sodium lauriminodipropionate, sodium cocamphopropionate, disodium cocoamphodipropionate, and cocoamphocarboxypropionate), and combinations thereof. In addition, pseudo amphoteric (ampholytic) surfactants such as betaines can also be used, including cocamidopropyl, coco, oleamidopropyl, or the like, or combinations thereof.

As to particular embodiments, the amount of citral ($C_{10}H_{16}O$, CAS No: 5392-40-5) included in the inventive composition (1) can used impart to impart a flavoring or a lemon-like odor or to facilitate removal and for a period of time after use of the inventive composition (1) repel parasites including fleas, ticks, or the like, or combinations thereof. Citral can be included in an amount of about 0.001% to about 10% by weight percent of the inventive composition (1). The amount of citral can be selected from the group including or consisting of: between about 0.001% to about 1.0% by weight of said composition, between about 0.5% to about 1.5% by weight of said composition, between about 1.0% to about 2.0% by weight of said composition, between about 1.5% to about 2.5% by weight of said composition, between about 2.0% to about 3.0% by weight of said composition, between about 2.5% to about 3.5% by weight of said composition, between about 3.0% to about 4.0% by weight of said composition, between about 3.5% to about 4.5% by weight of said composition, between about 4.0% to about 5.0% by weight of said composition, between about 4.5% to about 5.5% by weight of said composition, between about 5.0% to about 6.0% by weight of said composition, between about 5.5% to about 6.5% by weight of said composition, between about 6.0% to about 7.0% by weight of said composition, between about 6.5% to about 7.5% by weight of said composition, between about 7.0% to about 8.0% by weight of said composition, between about 7.5% to about 8.5% by weight of said composition, between about 8.0% to about 9.0% by weight of said composition, between about 8.5% to about 9.5% by weight of said composition, and between about 9.0% to about 10.0% by weight of said composition.

As to particular embodiments, the citral can be a synthetic citral, obtained from Sigma-Aldrich, 3050 Spruce Street, St. Louis, Mo., USA, or the like, or from a plant source including or selected from the group consisting of: *Backhousia, Cymbopogon, Leptospermum, Litsea, Ocimum, Lindera, Calypranthes, Citrus, Aloysia, Eucalyptus*, and *Melissa*. Citral can be present in oils derived from plant species within these genera. Exemplary sources of citral-containing oil can include, but are not limited to, *Backhousia citriodora* (lemon myrtle), *Litsea citrata, Litsea cubeba* (May Chang), *Cymbopogon citratus* (lemongrass), *Leptospermum liversidgei* (lemon teatree), and *Ocimum gratissimum* (clove basil), or the like, or combinations thereof. However, any plant genus and species that contains citral may be utilized as a plant source of citral.

As to particular embodiments, the amount of chelating agent can include or be selected from the group consisting of: N,N-bis(carboxymethyl)-DL-alanine trisodium salt ($C_7H_8NNa_3O_6$, CAS No: 164462-16-2), tetrasodium ethylenediaminetetraacetate ($C_{10}H_{12}N_2O_8Na_4$, CAS No: 64-02-8), ethylenediamine tetraacetic acid ("EDTA"), EDTA($Na$)$_2$, EDTA($Na$)$_4$, hydroxyalkanoic acids such as lactic acid, acidic sodium hexametaphosphate, or the like, or combinations thereof. A chelating agent can be generally used in an amount of about 0.1% to about 5% by weight of the inventive composition (1). The amount of chelating agent can be selected from the group including or consisting of: between about 0.1% to about 1.0% by weight of said composition, between about 0.5% to about 1.5% by weight of said composition, between about 1.0% to about 2.0% by weight of said composition, between about 1.5% to about 2.5% by weight of said composition, between about 2.0% to about 3.0% by weight of said composition, between about 2.5% to about 3.5% by weight of said composition, between about 3.0% to about 4.0% by weight of said composition, between about 3.5% to about 4.5% by weight of said composition, and between about 4.0% to about 5.0% by weight of said composition.

Again referring primarily to FIG. 2 and Table 1 below, an exemplary formulation of an inventive composition (1) useful for reducing, removing, or eliminating extraneous matter such as undesirable materials (2), odors (3) or parasites (4) associated with the hair, fur or skin (5) of an animal (6) can be understood.

A water of the inventive composition (1) can comprise filtered, de-ionized, distilled, or otherwise filtered or purified water ($H_2O$, CAS No: 7732-18-5).

A surfactant of the inventive composition (1) can comprise polysorbate 20 ($C_{58}H_{114}O_{26}$, CAS No: 9005-64-5). The trade name Tween 20, a polysorbate 20 surfactant suitable for use in embodiments can be obtained from Croda Inc., 300-A Columbus Circle, Edison, N.J. 08837, USA.

A citral source of the inventive composition (1) can comprise lemongrass oil (CAS No: 8007-02-1), a citral-containing oil suitable for use in embodiments can be obtained from *Cymbopogon citratus* (lemongrass), available from Arylessence, Inc., 1091 Lake Drive, Marietta, Ga. 30066, USA.

A chelating agent of the inventive composition (1) can comprise a trisodium salt of methylglycinediacetic acid ($C_7H_8NNa_3O_6$, CAS No: 164462-16-2). The trade name Trilon M Liquid, an aqueous solution of the trisodium salt of methylglycinediacetic acid suitable for use in embodiments can be obtained from BASF Corporation, 100 Park Avenue, Florham Park, N.J. 07932, USA.

Now referring primarily to FIG. 3 and Table 2 below, an exemplary formulation of an inventive composition (1) useful for reducing, removing, or eliminating extraneous matter such as undesirable materials (2), odors (3) or parasites (4) associated with the hair, fur or skin (5) of an animal (6) can be understood.

TABLE 2

| Raw Material | Weight Percent | Range Percent |
|---|---|---|
| Water | 98.56 | 80.00 to 99.97 |
| Surfactant | 1.000 | 0.100 to 5.000 |
| Lemongrass oil containing citral | 0.040 | 0.010 to 10.00 |
| Chelating agent | 0.400 | 0.100 to 5.000 |
| Coating agent | 1.500 | 0.100 to 10.00 |
| Conditioning agent | 7.250 | 0.100 to 20.00 |
| Preservative | 0.100 | 0.001 to 5.000 |
| Fragrance | 0.015 | 0.000 to 1.000 |
| Coloring agent | 0.015 | 0.000 to 1.000 |
| pH control agent | 0.010 | 0.000 to 1.000 |

A water of the inventive composition (1) can comprise filtered, de-ionized, distilled, or otherwise filtered or purified water ($H_2O$, CAS No: 7732-18-5).

A surfactant of the inventive composition (1) can comprise polysorbate 20 ($C_{58}H_{114}O_{26}$, CAS No: 9005-64-5). The trade name Tween 20, a polysorbate 20 surfactant suitable for use in embodiments can be obtained from Croda Inc., 300-A Columbus Circle, Edison, N.J. 08837, USA.

A citral source of the inventive composition (1) can comprise lemongrass oil (CAS No: 8007-02-1), a citral-containing oil suitable for use in embodiments can be obtained from *Cymbopogon citratus* (lemongrass), available from Arylessence, Inc., 1091 Lake Drive, Marietta, Ga. 30066, USA.

A chelating agent of the inventive composition (1) can comprise a trisodium salt of methylglycinediacetic acid ($C_7H_8NNa_3O_6$, CAS No: 164462-16-2). The trade name Trilon M Liquid, an aqueous solution of the trisodium salt of methylglycinediacetic acid suitable for use in embodiments can be obtained from BASF Corporation, 100 Park Avenue, Florham Park, N.J. 07932, USA.

Again referring to FIG. 3 and Table 2, as to particular embodiments, the inventive composition (1) can further include an amount of coating agent, which can function to coat the hair, fur or skin (5) of an animal (6). The coating agent can coat the hair, fur or skin (5) of an animal (6) to in part reduce or eliminate dryness imparted by use of the other chemicals or ingredients utilized in the inventive composition (1). Additionally, the coating agent can coat the cuticle of the hair or fur which can correspondingly alter the reflective properties of the hair or fur of an animal (6), to impart a sheen or glossy appearance to the hair or fur of the animal (6).

Exemplary coating agents can comprise compounds that are chemically similar to sebum, including, as illustrative examples, silicone or balsam oil obtained from *Abies balsamea*. A coating agent can be generally used in an amount of about 0.1% to about 10% by weight of the inventive composition (1). The amount of coating agent can be selected from the group including or consisting of: between about 0.1% to about 1.0% by weight of said composition, between about 0.5% to about 1.5% by weight of said composition, between about 1.0% to about 2.0% by weight of said composition, between about 1.5% to about 2.5% by weight of said composition, between about 2.0% to about 3.0% by weight of said composition, between about 2.5% to about 3.5% by weight of said composition, between about 3.0% to about 4.0% by weight of said composition, between about 3.5% to about 4.5% by weight of said composition, between about 4.0% to about 5.0% by weight of said composition, between about 4.5% to about 5.5% by weight of said composition, between about 5.0% to about 6.0% by weight of said composition, between about 5.5% to about 6.5% by weight of said composition, between about 6.0% to about 7.0% by weight of said composition, between about 6.5% to about 7.5% by weight of said composition, between about 7.0% to about 8.0% by weight of said composition, between about 7.5% to about 8.5% by weight of said composition, between about 8.0% to about 9.0% by weight of said composition, between about 8.5% to about 9.5% by weight of said composition, and between about 9.0% to about 10.0% by weight of said composition. As an illustrative example, an inventive composition (1) can include about 1.5% by weight of a coating agent comprising silicone.

As to other particular embodiments, the inventive composition (1) can further include an amount of conditioning agent, which can be useful in making the hair, fur or skin (5) of an animal (6) less tangled and more readily combed. A conditioning agent can comprise hydrophobic conditioning agents, hydrophilic conditioning agents, structured conditioning agent, or the like, or combinations thereof.

Exemplary conditioning agents can include or be selected from the group consisting of: *aloe* extracts, jojoba oil, propylene glycol ($C_3H_8O_2$, CAS No: 57-55-6), or the like, or combinations thereof. The conditioning agent can be generally used in an amount of about 0.1% to about 20% by weight percent of the composition (1). The amount of conditioning agent can be selected from the group including or consisting of: between about 0.1% to about 2.0% by weight of said composition, between about 1.0% to about 3.0% by weight of said composition, between about 2.0% to about 4.0% by weight of said composition, between about 3.0% to about 5.0% by weight of said composition, between about 4.0% to about 6.0% by weight of said composition, between about 5.0% to about 7.0% by weight of said composition, between about 6.0% to about 8.0% by weight of said composition, between about 7.0% to about 9.0% by weight of said composition, between about 8.0% to about 10.0% by weight of said composition, between about 9.0% to about 11.0% by weight of said composition, between about 10.0% to about 12.0% by weight of said composition, between about 11.0% to about 13.0% by weight of said composition, between about 12.0% to about 14.0% by weight of said composition, between about 13.0% to about 15.0% by weight of said composition, between about 14.0% to about 16.0% by weight of said composition, between about 15.0% to about 17.0% by weight of said composition, between about 16.0% to about 18.0% by weight of said composition, between about 17.0% to about 19.0% by weight of said composition, and between about 18.0% to about 20.0% by weight of said composition. As an illustrative example, an embodiment of the inventive composition (1) can include 7.05% by weight of propylene glycol.

As to other particular embodiments, the inventive composition (1) can further include an amount of preservative, which can be utilized to prevent decomposition during the normal storage duration of the inventive composition (1) by microbial growth, chemical alterations, or the like, or combinations thereof. Illustrative examples of preservatives include or can be selected from the group consisting of: 5-chloro-2-methyl-4-isothiazolin-3-one (CAS No: 26172-55-4), 2-methyl-4-isothiazolin-3-one (CAS No: 2682-20-4), 1-(3-chloroallyl)-3,5,7-triaza-1-azoniaadamantane chloride ($C_9H_{16}Cl_2N_4$, CAS No: 4080-31-3), hexamethylenetramine ($C_6H_{12}N_4$, CAS No: 100-97-0), 1,3-dichloropropene ($C_3H_4Cl_2$, CAS No: 542-75-6), dichloromethane ($CH_2Cl_2$, CAS No: 75-09-2), sodium bicarbonate ($CHNaO_3$, CAS No: 144-55-8), sodium benzoate, parabens, 1,3-bis (hydroxymethyl)-5,5-dimethylimidazolidine-2,4-dione, tetrasodium EDTA, and chloroallylhexaminium chloride, or the like, or combinations thereof. A preservative can be included in an amount of about 0.001% to about 5% by weight percent of the composition (1). The amount of preservative can be selected from the group including or consisting of: between about 0.001% to about 1.0% by weight of said composition, between about 0.5% to about 1.5% by weight of said composition, between about 1.0% to about 2.0% by weight of said composition, between about 1.5% to about 2.5% by weight of said composition, between about 2.0% to about 3.0% by weight of said composition, between about 2.5% to about 3.5% by weight of said composition, between about 3.0% to about 4.0% by weight of said composition, between about 3.5% to about 4.5% by weight of said composition, and between about 4.0% to about 5.0% by weight of said composition. As an illustrative example, an inventive composition (1) can include about 0.1% by weight of a preservative comprising 5-chloro-2-methyl-4-isothiazolin-3-one and 2-methyl-4-isothiazolin-3-one.

As to other particular embodiments, the inventive composition (1) can further include an amount of fragrance, which provides a scent to the inventive composition (1). A fragrance can be included in an amount between none and about 1.0% by weight of the composition (1). Certain embodiments omit fragrance while other embodiments can have a greater or lesser weight percent of between zero weight percent and about 1.0% by weight of the inventive composition (1), adjusted to achieve the desired fragrance or scent with the weight percent of all other raw materials adjusted accordingly. As an illustrative example, an inventive composition (1) can include 0.015% by weight of a fragrance comprising a synthetic citral 3,7-dimethyl-2,6-octadienal ($C_{10}H_{16}O$, CAS No: 5392-40-5).

As to other particular embodiments, the inventive composition (1) can further include an amount of coloring agent. The coloring agent can be included in an amount between none and about 1.0% by weight of the inventive composition (1). Certain embodiments omit a coloring agent while other embodiments can have a greater or lesser weight percent of between zero weight percent and about 1.0% by weight of the inventive composition (1), adjusted to achieve the desired color with the weight percent of all other raw materials adjusted accordingly. As an illustrative example, an inventive composition (1) can include 0.015% by weight of a coloring agent comprising a dye.

As to other particular embodiments, the inventive composition (1) can further include an amount of pH control agent, or the pH control agent can be used in sufficient amount, to adjust the inventive composition (1) pH to a predetermined pH. An inventive composition (1) pH can be in a range of between about 6.0 and about 10.0. The inventive composition (1) pH range can be selected from the group including or consisting of: between about 6.0 to about 7.0, between about 6.5 to about 7.5, between about 7.0 to about 8.0, between about 7.5 to about 8.5, between about 8.0 to about 9.0, between about 8.5 to about 9.5, and between about 9.0 to about 10.0. The pH control agent can be included in an amount between none and about 1.0% by weight of the inventive composition (1) to achieve or control pH of the inventive composition (1). Certain embodiments omit a pH control agent while other embodiments can have a greater or lesser weight percent of between zero weight percent and about 1.0% by weight of the inventive composition (1), adjusted to achieve the inventive composition (1) pH. As an illustrative example, the pH control agent can include 0.01% by weight of a pH control agent such as citric acid or sodium bicarbonate.

An inventive composition (1) of the present invention can be produced by combining two or more of the above-described inventive composition (1) components; however, the instant invention can further include additional chemicals or ingredients combined with the above-described embodiments of the inventive composition (1). As used herein, the term "combination or combining" refers to any method of putting two or more materials together. Such methods include, but are not limited to, mixing, blending, commingling, concocting, homogenizing, ultrasonic homogenizing, incorporating, intermingling, fusing, joining, shuffling, stirring, coalescing, integrating, confounding, joining, uniting, creating a stable suspension of two immiscible liquids via any number of means such as emulsions, or the like. As an exemplary embodiment, an inventive composition (1) can be produced by combining 98.56% by weight of water and 1.0% by weight of surfactant and 0.04% by weight of lemongrass oil and 0.4% by weight of chelating agent.

Now referring primarily to FIG. 4 and Table 3 below, an exemplary embodiment of the inventive composition (1) useful for reducing, removing, or eliminating materials (2), odors (3) or parasites (4) associated with the hair, fur or skin (5) of an animal (6) can be understood.

TABLE 3

| Raw Material | Weight Percent | Range Percent |
|---|---|---|
| Water | 89.695 | 68.85 to 98.12 |
| Trilon M Liquid | 0.400 | 0.200 to 0.600 |
| Arylessence Mod AF 151615 | 0.015 | 0.005 to 0.200 |
| Lemongrass oil | 0.040 | 0.010 to 0.500 |
| Tween 20 | 0.500 | 0.100 to 1.000 |
| Ethox DO-9 | 0.500 | 0.300 to 2.000 |
| Masil EM 10000 C | 1.500 | 0.200 to 10.00 |
| Jojoba oil | 0.100 | 0.050 to 0.200 |
| Propylene glycol | 7.050 | 1.000 to 15.00 |
| Actisea 100 | 0.100 | 0.010 to 1.500 |
| KATHON CG/ICP | 0.100 | 0.005 to 0.150 |

A water of the inventive composition (1) can comprise filtered, de-ionized, distilled, or otherwise filtered or purified water ($H_2O$, CAS No: 7732-18-5).

A chelating agent of the inventive composition (1) can comprise a trisodium salt of methylglycinediacetic acid ($C_7H_8NNa_3O_6$, CAS No: 164462-16-2). The trade name Trilon M Liquid, an aqueous solution of the trisodium salt of methylglycinediacetic acid suitable for use in embodiments can be obtained from BASF Corporation, 100 Park Avenue, Florham Park, N.J. 07932, USA.

A citral source of the inventive composition (1) can comprise a fragrance with the trade name Arylessence Mod AF 151615, including a synthetic citral 3,7-dimethyl-2,6-octadienal ($C_{10}H_{16}O$, CAS No: 5392-40-5), available from Arylessence, Inc., 1091 Lake Drive, Marietta, Ga. 30066, USA. Particular embodiments may use other fragrances or no fragrance without a substantive change in the function of the inventive composition (1). Weight percentages can be adjusted correspondingly.

A citral source of the inventive composition (1) can comprise lemongrass oil (CAS No: 8007-02-1), a citral-containing oil suitable for use in embodiments can be obtained from *Cymbopogon citratus* (lemongrass), available from Arylessence, Inc., 1091 Lake Drive, Marietta, Ga. 30066, USA.

A surfactant of the inventive composition (1) can comprise polysorbate 20 ($C_{58}H_{114}O_{26}$, CAS No: 9005-64-5). The trade name Tween 20, a polysorbate 20 surfactant suitable for use in embodiments can be obtained from Croda Inc., 300-A Columbus Circle, Edison, N.J. 08837, USA.

A surfactant of the inventive composition (1) can comprise poly(ethylene glycol)dioleate ($C_{20}H_{40}O_4$, CAS No: 9005-07-6). The trade name Ethox DO-9, a poly(ethylene glycol)dioleate ester suitable for use in embodiments can be obtained from Ethox Chemicals, LLC, 1801 Perimeter Road, Greensville, S.C. 29605, USA.

A coating agent of the inventive composition (1) can comprise silicone, including polydimethylsiloxane $((C_2H_6OSi)_n$, CAS No: 63148-62-9). The trade name Masil EM 10000C, a polydimethylsiloxane emulsion suitable for use in embodiments can be obtained from Emerald Performance Materials, 2020 Front Street, Suite 100, Cuyahoga Falls, Ohio 44221, USA.

A conditioning agent of the inventive composition (1) can comprise jojoba oil (CAS No: 61789-91-1), a liquid wax obtained from the seed of *Simmondsia chinensis* (jojoba) suitable for use in embodiments can be obtained from Arylessence, Inc., 1091 Lake Drive, Marietta, Ga. 30066, USA.

A conditioning agent of the inventive composition (1) can comprise propylene glycol ($C_3H_8O_2$, CAS No: 57-55-6) suitable for use in embodiments can be obtained from Dow Chemical Company, 2030 Dow Center Midland, Mich. 48674, USA.

A conditioning agent of the inventive composition (1) can comprise *aloe* including *Aloe barbadensis* extract (CAS No: 94349-62-9). The trade name Actisea 100, a concentrated extract from selected marine algae and the inner gel of *Aloe barbadensis* suitable for use in embodiments can be obtained from Active Organics, 1097 Yates Street, Lewisville, Tex. 75057, USA.

A preservative of the inventive composition (1) can comprise 5-chloro-2-methyl-4-isothiazolin-3-one ($C_4H_4ClNOS$, CAS No: 26172-55-4) and 2-methyl-4-isothiazolin-3-one ($C_4H_5NOS$, CAS No: 2682-20-4). The trade name KATHON CG/ICP, containing active ingredients including 5-chloro-2-methyl-4-isothiazolin-3-one (CAS No: 26172-55-4) and 2-methyl-4-isothiazolin-3-one (CAS No: 2682-20-4), and inert ingredients including magnesium chloride ($MgCl_2$, CAS No: 7786-30-3), magnesium nitrate ($Mg(NO_3)_2$, CAS No: 10377-60-3), and cupric nitrate ($Cu(NO_3)_2 \cdot 3H_2O$, CAS No: 10031-43-3) suitable for use in embodiments can be obtained from Dow Chemical Company, 2030 Dow Center Midland, Mich. 48674, USA.

An illustrative embodiment of the inventive composition (1) can be produced by mixing for about fifteen minutes the combination of about 89.695% by weight of water; about 0.400% by weight of Trilon M Liquid; about 0.015% by weight of Arylessence Mod AF 151615; about 0.040% by weight of lemongrass oil; about 0.100% by weight of jojoba oil; and 0.500% by weight of Tween 20; and 0.500% by weight of Ethox DO-9, (hereinafter referred to as "Combination A"). Following, Combination A can be combined with about 1.500% by weight of Masil EM 10000C (hereinafter referred to as "Combination B"). Following, Combination B can be combined with about 7.050% by weight of propylene glycol; and 0.100% by weight of Actisea 100 (hereinafter referred to as "Combination C"). Following, Combination C can be combined by mixing for about sixty minutes with about 0.100% by weight of KATHON CG/ICP (hereinafter referred to as "Combination D"). Following, Combination D can be combined with an amount of pH control agent sufficient to provide an inventive composition (1) having an inventive composition (1) pH in a range of between about 6.5 and about 7.5. As to a particular embodiment, Combination D can be combined with an amount of pH control agent sufficient to provide an inventive composition (1) having an inventive composition (1) pH of about 7.0.

Now referring primarily to FIG. 5 and Table 4 below, an exemplary formulation of an inventive composition (1) useful for reducing, removing, or eliminating materials (2), odors (3) or parasites (4) associated with the hair, fur or skin (5) of an animal (6) can be understood.

TABLE 4

| Raw Material | Weight Percent | Range Percent |
| --- | --- | --- |
| Water | 90.36 | 71.10 to 98.56 |
| VERSENE 100 Chelating Agent | 0.250 | 0.050 to 0.600 |
| Arylessence Mod AF 151615 | 0.040 | 0.010 to 0.400 |
| Tween 20 | 0.500 | 0.100 to 1.000 |
| Dow Corning 200 Fluid | 1.500 | 0.200 to 10.00 |
| Jojoba oil | 0.100 | 0.050 to 0.200 |
| Propylene glycol | 7.050 | 1.000 to 15.00 |
| Actisea 100 | 0.100 | 0.010 to 1.500 |
| DOWICIL 75 Preservative | 0.100 | 0.020 to 0.200 |

A water of the inventive composition (1) can comprise filtered, de-ionized, distilled, or otherwise filtered or purified water ($H_2O$, CAS No: 7732-18-5).

A chelating agent of the inventive composition (1) can comprise a trisodium salt of methylglycinediacetic acid ($C_7H_8NNa_3O_6$, CAS No: 164462-16-2). The trade name Trilon M Liquid, an aqueous solution of the trisodium salt of methylglycinediacetic acid suitable for use in embodiments can be obtained from BASF Corporation, 100 Park Avenue, Florham Park, N.J. 07932, USA.

A citral source of the inventive composition (1) can comprise a fragrance with the trade name Arylessence Mod AF 151615, including a synthetic citral 3,7-dimethyl-2,6-octadienal ($C_{10}H_{16}O$, CAS No: 5392-40-5), available from Arylessence, Inc., 1091 Lake Drive, Marietta, Ga. 30066, USA. Particular embodiments may use other fragrances or no fragrance without a substantive change in the function of the inventive composition (1). Weight percentages can be adjusted correspondingly.

A surfactant of the inventive composition (1) can comprise polysorbate 20 ($C_{58}H_{114}O_{26}$, CAS No: 9005-64-5). The trade name Tween 20, a polysorbate 20 surfactant suitable for use in embodiments can be obtained from Croda Inc., 300-A Columbus Circle, Edison, N.J. 08837, USA.

A coating agent of the inventive composition (1) can comprise silicone, including polydimethylsiloxane $((C_2H_6OSi)_n$, CAS No: 63148-62-9). The trade name Dow Corning 200 Fluid, a polydimethylsiloxane fluid, can be obtained from Dow Chemical Company, 2030 Dow Center Midland, Mich. 48674, USA.

A conditioning agent of the inventive composition (1) can comprise jojoba oil (CAS No: 61789-91-1), a liquid wax obtained from the seed of *Simmondsia chinensis* (jojoba) suitable for use in embodiments can be obtained from Arylessence, Inc., 1091 Lake Drive, Marietta, Ga. 30066, USA.

A conditioning agent of the inventive composition (1) can comprise propylene glycol ($C_3H_8O_2$, CAS No: 57-55-6) suitable for use in embodiments can be obtained from Dow Chemical Company, 2030 Dow Center Midland, Mich. 48674, USA.

A conditioning agent of the inventive composition (1) can comprise *aloe* including *Aloe barbadensis* extract (CAS No: 94349-62-9). The trade name Actisea 100, a concentrated extract from selected marine algae and the inner gel of *Aloe barbadensis* suitable for use in embodiments can be obtained from Active Organics, 1097 Yates Street, Lewisville, Tex. 75057, USA.

A preservative of the inventive composition (1) can comprise 1-(3-chloroallyl)-3,5,7-triaza-1-azoniaadamantane chloride ($C_9H_{16}Cl_2N_4$, CAS No: 4080-31-3), hexamethylenetetramine ($C_6H_{12}N_4$, CAS No: 100-97-0), 1,3-dichloropropene ($C_3H_4Cl_2$, CAS No: 542-75-6), dichloromethane ($CH_2Cl_2$, CAS No: 75-09-2), and sodium bicarbonate ($CHNaO_3$, CAS No: 144-55-8). The trade name DOWICIL 75 Preservative, including 1-(3-chloroallyl)-3,5,7-triaza-1-azoniaadamantane chloride, hexamethylenetetramine, 1,3-dichloropropene, dichloromethane, and sodium bicarbonate can be obtained from Dow Chemical Company, 2030 Dow Center Midland, Mich. 48674, USA.

An illustrative embodiment of the inventive composition (1) can be produced by mixing for about sixty minutes about 90.36% by weight of $H_2O$; about 0.250% by weight of VERSENE 100 Chelating Agent; about 0.040% by weight of Arylessence Mod AF 151615; about 0.500% by weight of Tween 20; about 1.500% by weight of Dow Corning 200 Fluid; about 0.100% by weight of jojoba oil; about 7.050% by weight of propylene glycol; about 0.100% by weight of Actisea 100; and about 0.100% by weight of DOWICIL 75 Preservative.

While particular formulations for an inventive composition (1) are set out above, the weight percentages can vary substantially to produce a wide range of formulations using the same chemicals, ingredients, or raw materials (or by adding additional types of raw materials to the raw materials listed) to address a variety of applications while retaining a desired level of efficacy of the inventive composition (1) as an inventive composition for animals.

As can be easily understood from the foregoing, the basic concepts of the present invention may be embodied in a variety of ways. The invention involves numerous and varied embodiments of a composition and methods for making and using such compositions including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "combination" should be understood to encompass disclosure of the act of "combining"—whether explicitly discussed or not—and, conversely, were there effectively disclosure of the act of "combining", such a disclosure should be understood to encompass disclosure of a "combination" and even a "means for combining." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Generally, as to each of the formulations set out in Table 1 through Table 4 and FIG. 2 through FIG. 5, or any table or figure herein, each particular weight percent value shall not be interpreted solely as an absolute value and each particular weight percent value as to each raw material will be interpreted as having a range between a first particular weight percent value and a second particular weight percent value based upon variation in the preparation of the formulation. These ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicants should be understood to claim at least: i) each of the inventive compositions herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A composition comprising:
    an amount of water;
    an amount of chelating agent;
    an amount of surfactant, wherein said amount of surfactant comprises a combination of polysorbate 20 and a polyethylene glycol) dioleate ester between about 0.1% to about 5% by weight of said composition; and
    an amount of polydimethylsiloxane of between about 0.2% to about 10%, said composition comprises an emulsion;
    and an amount of citral containing oil of between about 0.001% to about 10% by weight of said composition.

2. The composition of claim 1, wherein said amount of surfactant is selected from the group consisting of: between about 0.1% to about 1.0% by weight of said composition, between about 0.5% to about 1.5% by weight of said composition, between about 1.0% to about 2.0% by weight of said composition, between about 1.5% to about 2.5% by weight of said composition, between about 2.0% to about 3.0% by weight of said composition, between about 2.5% to about 3.5% by weight of said composition, between about 3.0% to about 4.0% by weight of said composition, between about 3.5% to about 4.5% by weight of said composition, and between about 4.0% to about 5.0% by weight of said composition.

3. The composition of claim 1, wherein said amount of citral is from a source selected from the group consisting of: *Backhousia, Cymbopogon, Leptospermum, Litsea, Ocimum, Lindera, Calypranthes, Citrus, Aloysia, Eucalyptus,* and *Melissa*, or combinations thereof.

4. The composition of claim 1, wherein said amount of polydimethylsiloxane comprises between about 0.2% to about 1.5%.

5. The composition of claim 1, wherein said amount of chelating agent comprising comprises a trisodium salt of methylglycinediacetic acid.

6. The composition of claim 1, wherein said surfactant consists of said combination of polysorbate 20 and a poly (ethylene glycol) dioleate ester between about 0.1% to about 5% by weight of said composition.

7. The composition of claim 1, further comprising an amount of conditioning agent.

8. The composition of claim 7, wherein said amount of conditioning agent comprises propylene glycol.

9. The composition of claim 7, wherein said amount of conditioning agent comprises jojoba oil.

10. The composition of claim 7, wherein said amount of conditioning agent comprises *aloe*.

11. The composition of claim 1, further comprising an amount of preservative.

* * * * *